United States Patent [19]

Fischer

[11] Plant 4,115

[45] Sept. 27, 1977

[54] AFRICAN VIOLET PLANT NAMED ABBY

[75] Inventor: Arnold W. Fischer, Fallbrook, Calif.

[73] Assignee: Geo. J. Ball, Inc., West Chicago, Ill.

[21] Appl. No.: 730,664

[22] Filed: Oct. 7, 1976

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Rummler and Snow

[57] ABSTRACT

A new and distinct variety of African violet plant for potted plant culture distinguished by its large white flowers which, in general, are uniquely arranged in a circular pattern, by its ability to produce exceptionally large, abundant and attractive foliage, and by its recurrent to continuous year around blooming habit.

1 Drawing Figure

BACKGROUND OF THE NEW PLANT

My new variety of African violet plant originated as a seedling of unknown parentage and was discovered by me in 1973 at Hanover, Germany, among random pollinated plants being grown by me in the course of breeding efforts carried on with the object of developing a good white violet. This plant was selected for propagation because of its large white flowers and its lush production of large and attractive foliage and was asexually reproduced by me at Hanover, Germany, by means of leaf cuttings. Successive generations of this new plant, produced by leaf cuttings and division of shoots, have shown that its distinctive characteristics hold true from generation to generation and are firmly fixed and further propagation of this plant in the same manner at West Chicago, Ill., and at Woodburn, Oreg., U.S.A., has confirmed my observations.

DESCRIPTION OF THE DRAWING

My new variety of white African violet is illustrated by the accompanying full color photographic drawing which shows in one view a typical potted plant in full bloom and in another view a series of the flowers, in full face display, showing the variations of coloration that may occur according to plant culture.

DESCRIPTION OF THE NEW PLANT

The following is a detailed description of my new African violet plant as observed at West Chicago, Ill., with the color designations according to the R.H.S. Colour Chart published by The Royal Horticultural Society of London, England.

THE PLANT

Origin: Seedling.
Parentage: Unknown.
Classification:
*Botanic.*—*Saintpaulia ionantha.*
*Commercial.*—African Violet for pot culture.
Form: Compact potted plant, but more open than many violet varieties such as Eva (P.P. 3,611).
Height: 3 to 4 inches from soil line to top of flower, and 1 to 2 inches from soil to top of plant.
Growth: Condensed, with moderate vigor and with fairly strong petioles which spread horizontally.
Foliage: Abundant in quantity, the number of leaves being variable.
*Size of mature leaf.*—Length — 3 to 3½ inches, average 3¼ inches. Width — 2½ to 3½ inches, average 3 inches.
*Shape of leaf.*—Orbicular with a sagittate base, an acute to obtuse apex, and crenate margins.
*Texture.*—Velutinous.
*Venation.*—Pinnately veined and pronounced on the under side.
*Color.*—Upper side — Green 137C. Under side — Greyed Green 194D.
*Petioles.*—2 to 3 inches long, varying with the age of the plant and averaging 2½ inches.

THE BUD

Form: Globular, becoming urn-shaped as it opens.
Size: About ¼ inch in diameter just before opening.
Opening rate: Slow — 2 to 4 weeks from visible bud to opened flower.
Color:
*When sepals first divide.*—Yellow-Green 145D.
*When petals begin to unfurl.*—White 155C.
Sepals: Hooded over bud for a very short period.
*Form.*—Spear-shaped, upstanding and unbranched, with light curl-back but appressed to petals.
*Size.*—1/32 to 1/16 inch wide, 3/16 inch long.
*Color.*—Inside — Yellow-Green 145B. Outside — Yellow-Green 145B.
Calyx: Funnel-shaped and synsepalous.
*Size.*—⅜ to ½ inch wide.
*Splitting.*—Calyx splits to star shape.
*Aspect.*—Inside — smooth. Outside — hairy.
Peduncle: Length — 1½ to 2½ inches, averaging 2 inches.
*Strength.*—Strong and wiry but flexible.
*Aspect.*—Velutinous.
*Color.*—Yellow-Green 145C.

THE FLOWER

Blooming habit: Recurrent to continuous the year around with more flowers in spring and fall than otherwise.
Size of flower: Medium to large.
*Diameter.*—1 to 2 inches, average about 1½ inches.
*Depth.*—⅛ to ¼ inch, flat when open.
Shape of flower: Cup-shaped when bloom first opens, becoming flat when full open.
Borne: The inflorescence is cymose.
Petalage: Basally connate.

*Number.*—Mostly 5 when single with petaloid anthers. Occasionally 10 when fully double, also with petaloid anthers.

*Arrangement.*—Gamopetalous.

*Form.*—Rotate with ruffled petals, zygomorphic when single.

*Texture.*—Soft.

*Appearance.*—Glittery on upper side. Satiny on under side.

*Color.*—Upper side — Generally White 155D, but may tend to a Light Pink cast (Red-Purple 65D) depending upon culture. Reverse side — White 155D.

Petaloids: 1 to 4 petaloid anthers.

*Size.*—$\frac{1}{4}$ to $\frac{3}{8}$ inch.

*Color.*—White 155D.

Peduncle: Length — 2 to 3 inches, average $2\frac{1}{2}$ inches.

*Pedicels.*—About $\frac{3}{4}$ to 1 inch long.

*Strength.*—Sturdy and oblique to upright.

*Color.*—Yellow-Green 145C, tending toward 145B.

Discoloration after full bloom: Generally none but may Pink as flower gets older.

Effect of weather: Hot weather decreases the life of the flowers. Plants thrive in 70 to 80% relative humidity.

Persistence: Flowers hang on and turn brown at senescence.

Lasting quality: 7 to 10 days for fully opened flowers.

REPRODUCTIVE ORGANS

Stamens:

*Anthers.*—Number — 2 to 4 each with 2 anther cells. Arrangement: Basifixed, connate at apex.

Length: 1/16 to $\frac{1}{8}$ inch.

*Filaments.*—Length — $\frac{1}{8}$ to 3/16 inch. Color: White 155A.

*Pollen.*—Color — Yellow 7A.

Pistils: Number — One.

*Style.*—5/16 to $\frac{3}{8}$ inch long. Color: Green at base, becoming White then Light Pink at apex.

*Stigma.*—Color — White 155D.

Ovaries: Superior and velutinous.

*Note.*—The flowers of this plant are bisexual.

This new variety of African violet plant is particularly characterized by its production of truly clear, clean white flowers which are enhanced by a bed of heavy foliage of a lighter than usual green color. The flowers are generally uniquely arranged in a circular pattern, especially on younger plants, and the plant has the capability of producing an exceptionally large, lush and very attractive foliage base when supplied with ample humidity and lower light levels. This characteristic makes this plant a very worthy and decorative specimen even between flushes of bloom.

I claim:

1. A new and distinctive variety of African violet plant, substantially as herein shown and described, characterized by its relatively large and uniquely displayed white flowers which are borne on sturdy stems and arranged in a circular pattern above an abundant array of large foliage.

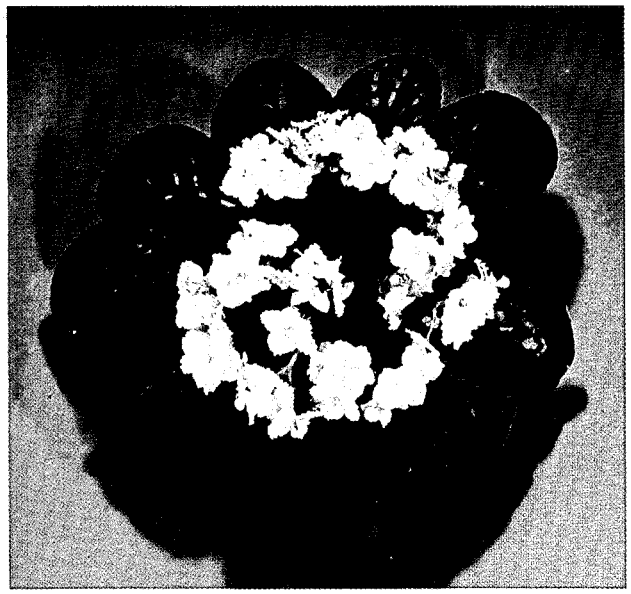
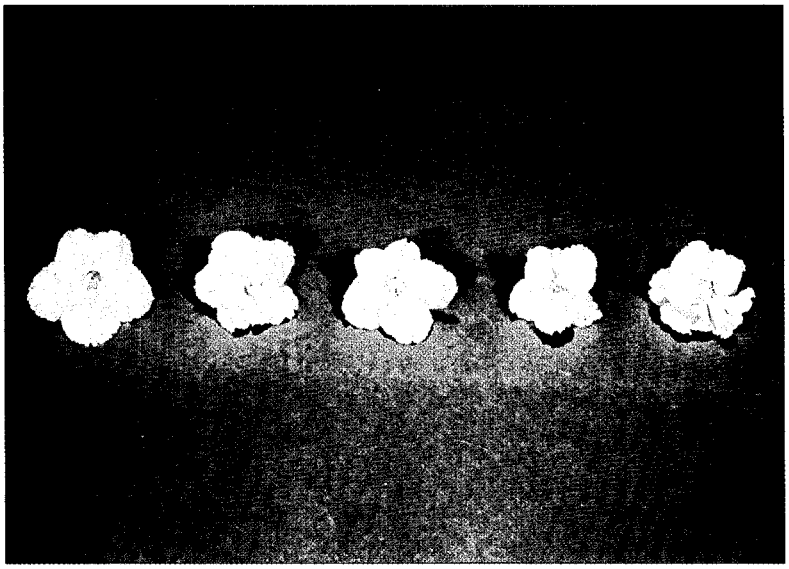

* * * * *